United States Patent
Pech et al.

(10) Patent No.: US 11,197,702 B2
(45) Date of Patent: Dec. 14, 2021

(54) SURGICAL BONE SCREW AND IMPLANT SYSTEM

(71) Applicant: ZIMMER GMBH, Winterthur (CH)

(72) Inventors: Uwe Pech, Tuttlingen (DE); Vladko Kotuljac, Schoemberg (DE)

(73) Assignee: ZIMMER GMBH, Winterthur (CH)

( * ) Notice: Subject to any disclaimer, the term of this patent is extended or adjusted under 35 U.S.C. 154(b) by 323 days.

(21) Appl. No.: 16/166,865

(22) Filed: Oct. 22, 2018

(65) Prior Publication Data

US 2019/0053837 A1 Feb. 21, 2019

Related U.S. Application Data

(63) Continuation of application No. 14/759,335, filed as application No. PCT/EP2014/050725 on Jan. 15, 2014, now Pat. No. 10,426,531.

(30) Foreign Application Priority Data

Jan. 15, 2013 (DE) .......................... 102013100362.1

(51) Int. Cl.
  *A61B 17/86* (2006.01)
  *A61B 17/80* (2006.01)

(52) U.S. Cl.
  CPC ........ *A61B 17/8057* (2013.01); *A61B 17/863* (2013.01); *A61B 17/8605* (2013.01); *A61B 17/866* (2013.01); *A61B 2017/8655* (2013.01)

(58) Field of Classification Search
  CPC ............ A61B 17/8057; A61B 17/8605; A61B 2017/8655
  See application file for complete search history.

(56) References Cited

U.S. PATENT DOCUMENTS

| 4,468,200 A | 8/1984 | Munch |
| 6,322,562 B1 | 11/2001 | Wolter |
| (Continued) |

FOREIGN PATENT DOCUMENTS

| DE | 3241963 C1 | 4/1984 |
| DE | 4343117 C2 | 11/1999 |
| (Continued) |

OTHER PUBLICATIONS

"U.S. Appl. No. 14/759,335, Advisory Action dated Apr. 20, 2018", 3 pgs.

(Continued)

*Primary Examiner* — Olivia C Chang
(74) *Attorney, Agent, or Firm* — Schwegman Lundberg & Woessner, P.A.

(57) ABSTRACT

The invention relates to a surgical bone screw comprising a shaft which has a bone thread and comprising a blocking means for interacting with a bone plate or for directly anchoring in the bone, in particular in the cortical bone. The surgical bone screw also comprises a screw head which has a rotationally symmetrical enveloping contour. The blocking means has a rib structure with at least one flank structure portion extending in the circumferential direction. According to the invention, the lateral surface of the enveloping contour has a constant or stepped concave progression, and the rib structure flank portion which extends in the circumferential direction is interrupted at least once in the circumferential direction, in particular multiple times, such that at least one elevation, in particular a plurality of elevations which are spaced in the circumferential direction, is produced in order to interact with the bone plate or with the bone in a blocking manner.

16 Claims, 7 Drawing Sheets

(56) References Cited

U.S. PATENT DOCUMENTS

Figure 10:
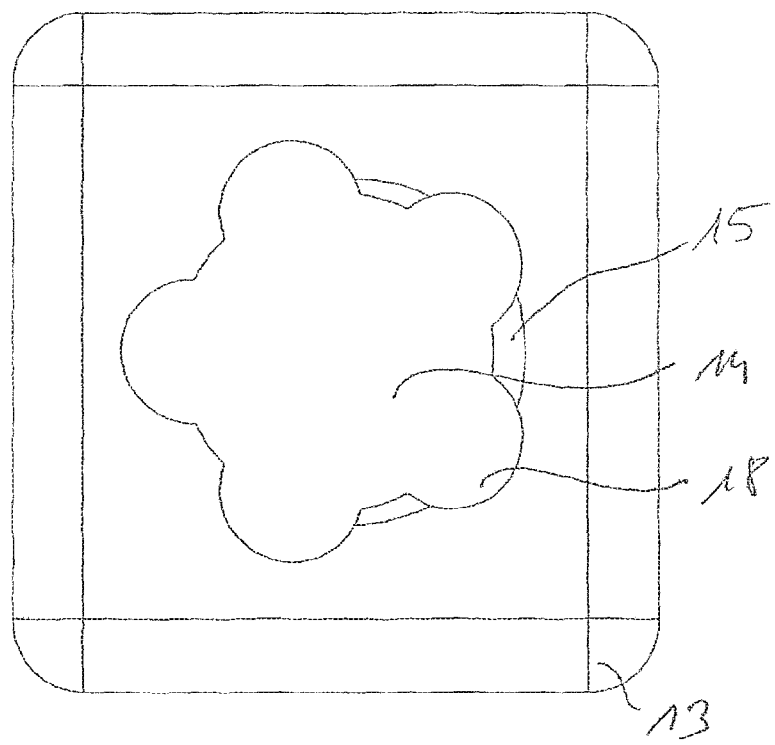

| | | |
|---|---|---|
| 10,426,531 B2 | 10/2019 | Pech et al. |
| 2005/0070904 A1 | 3/2005 | Gerlach et al. |
| 2006/0009771 A1 | 1/2006 | Orbay et al. |
| 2007/0043366 A1 | 2/2007 | Pfefferle et al. |
| 2007/0093837 A1 | 4/2007 | Bohrmann et al. |
| 2007/0162018 A1 | 7/2007 | Jensen et al. |
| 2007/0213728 A1 | 9/2007 | Lindemann et al. |
| 2008/0140130 A1 | 6/2008 | Chan et al. |
| 2009/0048605 A1 | 2/2009 | Yurek |
| 2009/0312803 A1* | 12/2009 | Austin ............... A61B 17/8014 606/305 |
| 2010/0312285 A1 | 12/2010 | White et al. |
| 2011/0106172 A1 | 5/2011 | Wallenstein et al. |
| 2011/0264149 A1 | 10/2011 | Pappalardo et al. |
| 2012/0083847 A1 | 4/2012 | Huebner et al. |
| 2014/0005728 A1* | 1/2014 | Koay .................. A61B 17/866 606/281 |
| 2014/0058455 A1* | 2/2014 | Appenzeller ...... A61B 17/8061 606/281 |
| 2015/0359575 A1 | 12/2015 | Pech et al. |

FOREIGN PATENT DOCUMENTS

| | | |
|---|---|---|
| DE | 202005014850 U1 | 2/2007 |
| DE | 102010038949 A1 | 2/2012 |
| EP | 1143867 B1 | 7/2002 |
| EP | 1273273 A2 | 1/2003 |
| EP | 1493399 A1 | 1/2005 |
| EP | 2147647 A1 | 1/2010 |
| FR | 2910800 A1 | 7/2008 |
| WO | WO-9709000 A1 | 3/1997 |
| WO | WO-2004086990 A1 | 10/2004 |
| WO | WO-2009023666 A2 | 2/2009 |
| WO | WO-2014111432 A1 | 7/2014 |

OTHER PUBLICATIONS

"U.S. Appl. No. 14/759,335, Final Office Action dated Jan. 17, 2018", 13 pgs.

"U.S. Appl. No. 14/759,335, Non Final Office Action dated Jul. 23, 2018", 16 pgs.

"U.S. Appl. No. 14/759,335, Non Final Office Action dated Aug. 15, 2017", 15 pgs.

"U.S. Appl. No. 14/759,335, Preliminary Amendment", 8 pgs.

"U.S. Appl. No. 14/759,335, Response filed Apr. 5, 2018 to Final Office Action dated Jan. 17, 2018", 17 pgs.

"U.S. Appl. No. 14/759,335, Response filed Nov. 15, 2017 to Non Final Office Action dated Aug. 15, 2017", 15 pgs.

"European Application Serial No. 18161579,0, European Search Report dated Jul. 2, 2018", 13 pgs.

"International Application Serial No. PCT/EP2014/050725, International Preliminary Report on Patentability dated Jul. 21, 2015", (W/ English Translation), 14 pgs.

"U.S. Appl. No. 14/759,335, Notice of Allowance dated Jan. 17, 2019", 5 pgs.

"U.S. Appl. No. 14/759,335, Notice of Allowance dated May 29, 2019", 5 pgs.

"U.S. Appl. No. 14/759,335, Response filed Oct. 23, 2018 to Non Final Office Action dated Jul. 23, 2018", 14 pgs.

"European Application Serial No. 18161579.0, European Search Report dated Oct. 16, 2018", (No English Translation), 13 pgs.

* cited by examiner

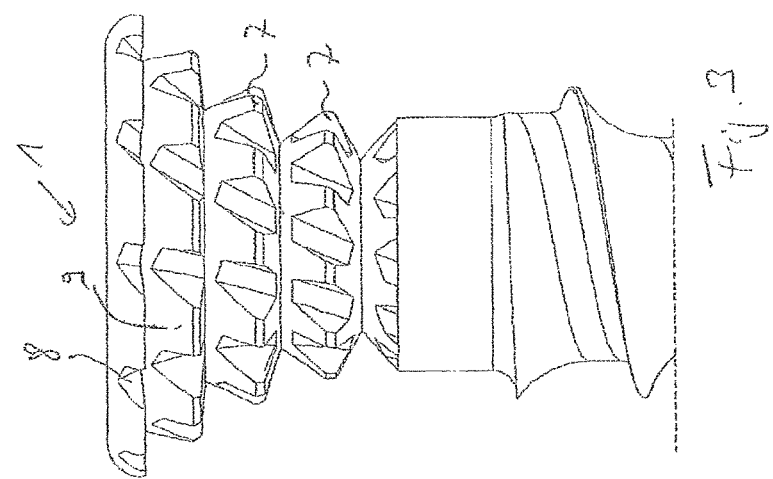
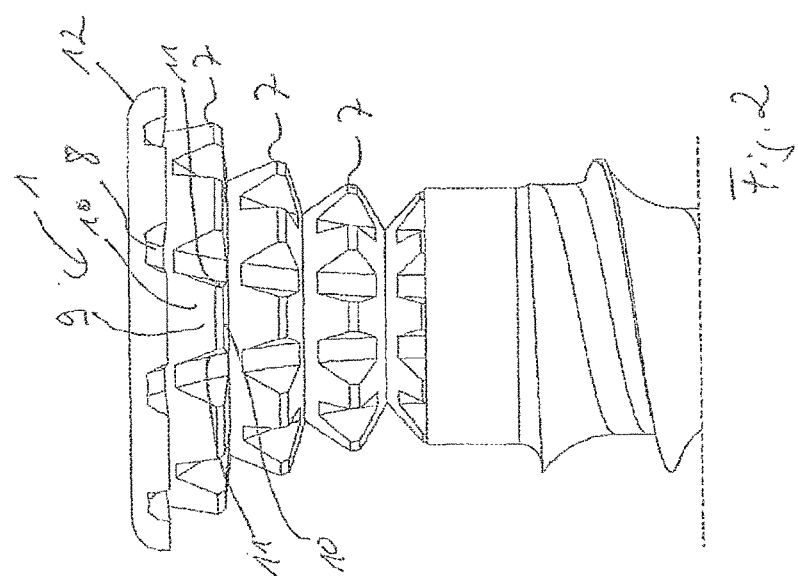
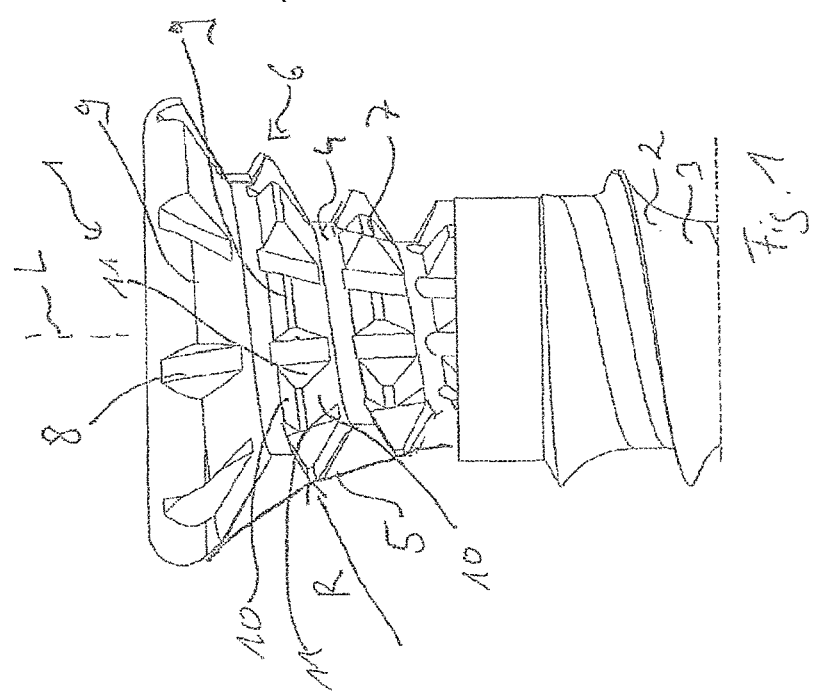

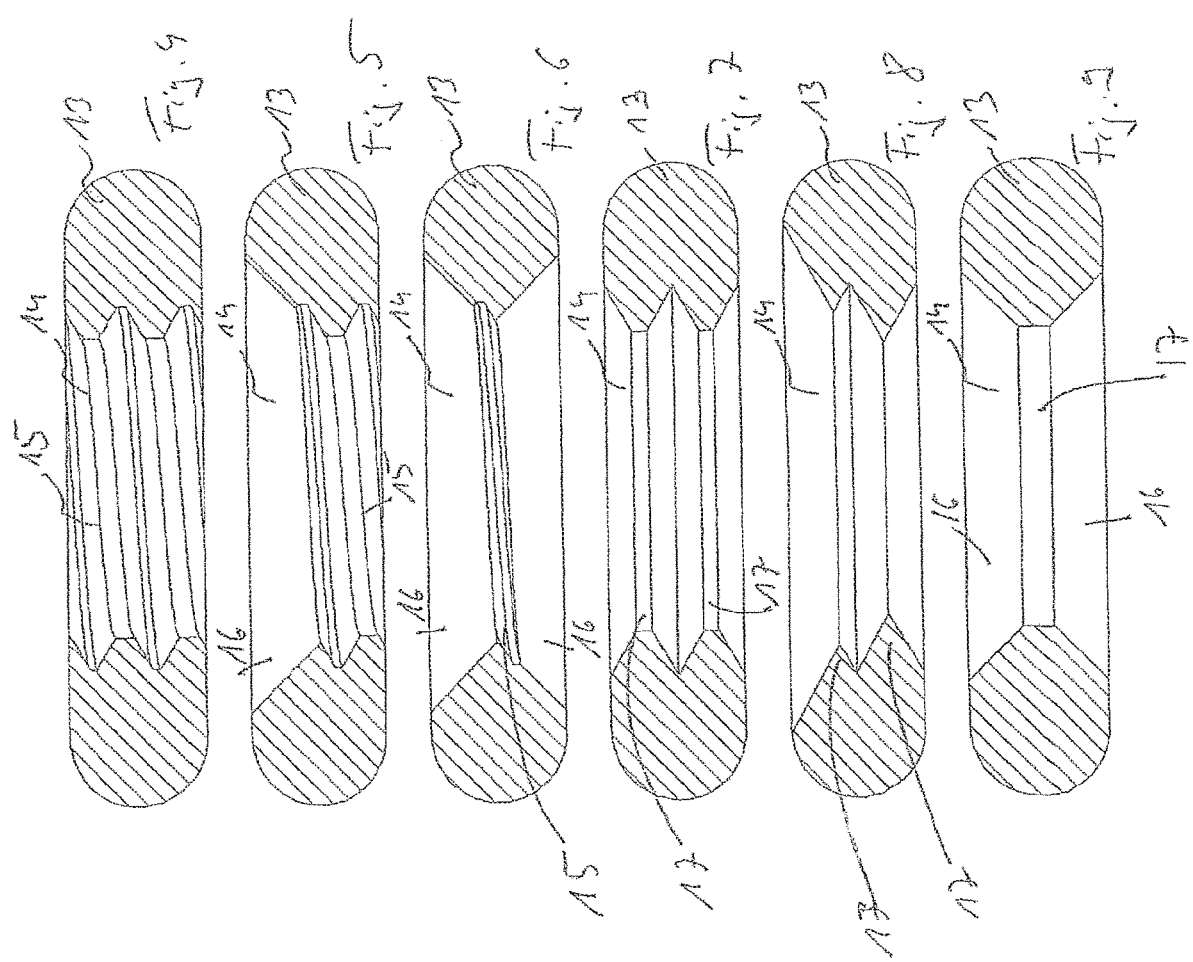

Fig. M

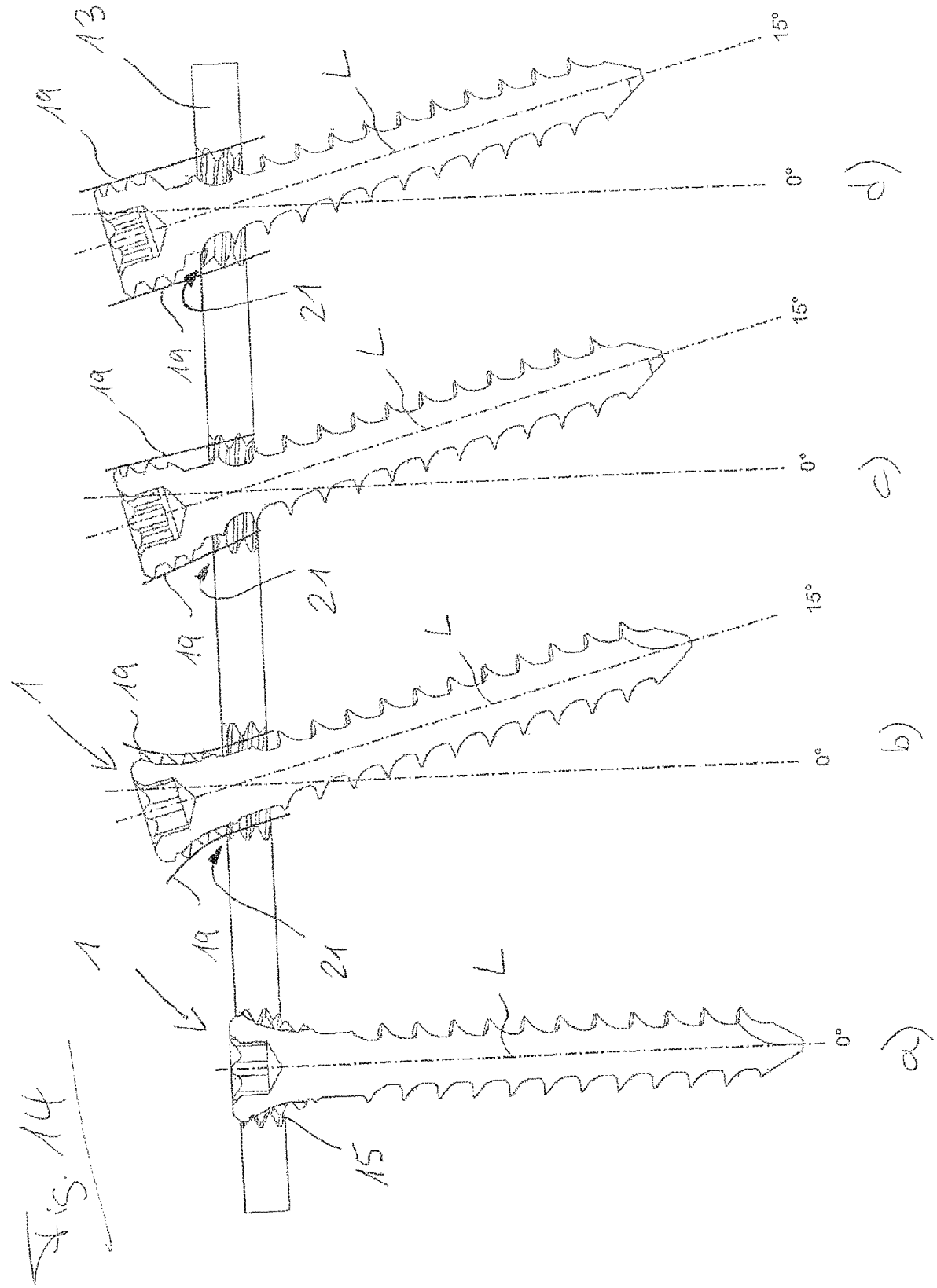

SURGICAL BONE SCREW AND IMPLANT SYSTEM

PRIORITY APPLICATIONS

This application is a continuation of U.S. patent application Ser. No. 14/759,335, filed on Jul. 6, 2015, which is a U.S. National Stage Filing under 35 U.S.C. 371 from International Application No. PCT/EP2014/050725, filed on 15 Jan. 2014, and published as WO/2014/111432 on 24 Jul. 2014, which application claims the benefit under 35 U.S.C. 119 to German Application No. 102013100362.1, filed on 15 Jan. 2013; which applications and publication are incorporated herein by reference in their entirety.

The invention relates to a surgical bone screw in accordance with claim 1.

So-called angle-stable fixation systems are used in surgery today, comprising a bone plate having at least one internally threaded hole as well as a bone screw which can be screwed into the internally threaded hole at different angles and which can be blocked by the bone plate.

Such an operational principle t is known, for example, from EP 1 143 867 B1. The known fixation system is based on the idea of generating a threaded connection between a bone screw and a bone plate by material shaping on the screwing in of the bone plate. It is disadvantageous in the known system that the connection of bone screw and bone plate tends to centering so that an intended angle of introduction can only be set or achieved with difficulty in practice.

Reference is additionally made to DE 43 43 117 C2.

An alternative fixation system is known from WO 2004/086990 A1. In the known bone screw, flattened portions are provided at the periphery of the non-rotationally symmetrical screw head which are spaced part in the peripheral direction, with the blocking resulting from a wedge clamping with the bone plate. The blocking effect also appears worthy of improvement here.

US 2005/0070904 A1, FR 2910800 A1, US 2007/162018 A1, US 2006/009771 A1, US 2008/140130 A1 and DE 20 2005 014850 U1 are named with respect to the further prior art.

It is the underlying object of the invention to introduce an improved bone screw which can also be introduced at large screwing angles of preferably more than 15°, in particular of 20°, and which is reliably fixable at this angle position. The bone screw should in this respect in particular be characterized by a comparatively easy introducibility and above all in that it engages fast, i.e. enters into a blocked interaction with the bone plate. Self-centering effects on the cooperation with a bone plate should in particular be avoided. The object further comprises providing an angle stable fixation system (implant system) having a correspondingly improved bone screw.

This object is satisfied with respect to the bone screw and with respect to the implant system (fixation system) by the features set forth in the description and the claims. Advantageous embodiments of the invention are also set forth in the description and the claims. All combinations of at least two features disclosed in the description, in the claims and/or in the Figures are covered within the framework of the invention.

The invention has recognized that it is necessary for the satisfaction of the above object to combine a concave enveloping contour of the screw head with an interrupted groove structure to ensure the desired effect of a secure holding of the bone screw in a bone plate at different angles or directly in the bone, in particular in the cortical bone. The concave enveloping contour in this respect brings about the effect in combination with the at least one elevated portion resulting from the interruption of the groove structure, more precisely of the flank structure section, in particular in combination with the plurality of elevated portions, of a fast and intimate contact between the elevated portions and the bone plate and can furthermore allow larger angles of introduction than in the prior art—in other words, a stable holding can be ensured by the combination of the at least one elevated portion and of the concavely rotationally symmetrical enveloping contour of the screw head even with comparatively large slanted positions or with large angles of introduction of the bone screw into the screw head.

In this respect, such a structure is in particular to be understood under the term "groove structure" which comprises one or more grooves which extend at least substantially in the peripheral direction.

When the bone screw is used with a bone plate, the screw head, i.e. the flank structure section of the groove structure, only impacts the edge of the thread formed in the passage opening of the bone plate at a larger angle of introduction with a concave enveloping contour than with a cylindrical or conical enveloping contour. In other words, the bone screw in accordance with the invention can be screwed in at larger angles than bone screws having a cylindrical or conical enveloping contour before there is the risk of a self-centration or of an uncontrolled pressing away of the plate or before a screwing into the plate is no longer possible at all due to the unwanted impact of the structure of the screw head onto the edge of the passage opening. This will be looked at in more detail at another point.

In this respect, the flank structure section is understood as an elongated (interrupted in accordance with the invention) raised contour which has two lateral flanks, in particular inclined with respect to one another (substantially facing in axial directions)—that is an (interrupted) bead which extends with or without a pitch and about the bone screw, in particular by more than one turn. The flank structure section will also simply be called a flank section in the following.

There are various possibilities with respect to the specific configuration of the rotationally symmetrical enveloping contour with its concave progression. It is thus possible to achieve a mathematically constant concave progression. The resulting enveloping contour can in this case be described by a curved mathematical function which is rotated about the central longitudinal axis of the bone screw (at a radial spacing therefrom). In an alternative embodiment, the enveloping contour can have a non-constant progression, i.e. a stepped or kinked progression, that is a non-constant transition between two concave or frustoconical sections, wherein the conical angle of the two axially mutually adjacent sections differs.

As will be explained later, the interruption of the groove structure, more precisely the raised flank structure section (bead section) of the groove structure which bounds a recess (groove) at at least one flank side, in particular at two flank sides results from the provision of a kind of notch or furrow which extends at an angle to the peripheral extent and which extends at least approximately in an axial direction in a projection onto a plane including the central longitudinal axis. A plurality of such notches are in particular arranged spaced apart from one another in the peripheral direction such that a plurality of raised portions result which are spaced apart in the peripheral direction. The screw can be screwed in particularly easily and engages particularly fast by the provision of a plurality of elevated portions. A breakout of the screw is avoided.

When an axial direction is spoken of in the following in conjunction with the longitudinal extent of the notches, an axial direction in the above-mentioned projection is to be understood hereby.

Provision is in particular made that elevated portions are not only located in one plane, but elevated portions spaced apart in the axial direction are also provided in addition to elevated portions spaced apart in the peripheral direction.

As will be explained below, provision is in particular made that the elevated portions have a pyramid-like or hipped-roof like contour or geometry. A shape is understood hereby in which the elevated portions have four flanks arranged at an angle with respect to one another and inclined in the direction toward an elevated portion center. A plurality of elevated portions spaced apart in the axial direction can result from the fact, in dependence on the embodiment of the groove structure or of the flank section, that a flank section coiled over more than one winding is provided or that two ring-shaped flank sections are provided which are in parallel with one another, which can be in mutually parallel radial planes or which can be arranged at an angle thereto, as will be explained below.

The elevated portions can also have a the shape of a truncated pyramid, a wedge shape or a frustoconical shape.

In addition to the use of the surgical bone screw in accordance with the invention in an angle stable implant system having a bone plane, the bone screw in accordance with the invention is also suitable for a direct anchorage in the bone due to the specific design of the bone screw, wherein the screw head cuts through the cortical bone by its at least one elevated portion, preferably by its plurality of elevated portions, and automatically anchors itself in the bone. The stability of the connection is further increased by a possible growing of the bone into a region between the elevated portions. In the aforesaid case, the bone screw can be used as a so-called intramedullary locking screw. It is also conceivable to provide the bone screw as a compression screw, wherein the bone screw should in this case have threads of mutually different pitches. Provision can in particular be made in this case that the groove structure of the screw head, in particular a plurality of elevated portions formed by the interruption of the flank structure section, forms/form an external thread whose pitch differs from the pitch of a thread of the screw shaft.

The screw formed in accordance with the concept of the invention can be formed from titanium, steel or plastic, in particular PEEK. In the case of the provision of a screw belonging to the bone plate, the bone plate can be formed either from the same material as the screw, but in particular from a different, softer material.

As initially mentioned, there are different possibilities with regard to the design of the groove structure. It can thus be formed in the manner of an external thread, that is such that the flank section is coiled, and indeed in the simplest case once around the screw head, wherein provision is made, in particular with a difficult manufacture, on the one hand, but to increase the number of supporting elements, on the other hand, that the coiled flank section extends over more than the simple screw head periphery, in particular over at least 1.5 times, in particular over at least twice or three times the periphery of the screw head. Provision is in particular made that the flank section passes through a peripheral angle with an axial spacing multiple times. Alternatively to a coiled flank section, it can also be formed free of pitch, that is it can form a ring interrupted by at least one interruption, wherein provision is in particular made that a plurality of such rings are provided which are in particular arranged in parallel with one another. In this respect, it is possible in accordance with a first alternative that the ring-shaped (interrupted) flank structure sections are in mutually parallel radial planes. The flank structure sections are circular in this case. In an alternative embodiment, the flank structure sections are oval and thus arranged at an angle to the aforesaid radial planes.

An embodiment of the bone screw is in particular provided in which the enveloping contour of the screw head, is configured as concave, in particular in an axially through-going manner, but at least over an axial section, in particular over the larger part of the axial extent of the screw head.

Provision is in particular made that, with a constant enveloping contour jacket surface progression, the concave shape describes or comprises a part arc of a circle in a longitudinal sectional view, wherein the radius of the part arc of the circle is in particular selected from a value range between 0.5 mm and 7 mm, in particular between 1 mm and 6 mm, in particular between 2 mm and 4 mm, and in particular amounts to least approximately 3 mm.

The enveloping contour can comprise at least two frustoconical sections or can be formed by at least two frustoconical sections, wherein the frustoconical sections in particular have mutually different conical angles.

In the initially described alternative embodiment with a non-constant enveloping contour, provision is in particular made that the frustoconical jacket surface sections form tangents at a part arc of a circle in a longitudinal sectional view, in particular with a radius from the previously named value ranges or with the previously named value.

Provision is in particular made that not only elevated portions spaced apart in the peripheral direction are provided, but that rather a plurality of axially spaced apart elevated portions, in particular two or more than two, are provided, in particular at at least one peripheral angle, which can be achieved, on the one hand, in that a coiled flank structure section extends about the screw head more than once in the peripheral direction or, on the other hand, in that at least two ring-shaped surface structure sections arranged in parallel with one another are provided which are each divided at least once, preferably a multiple of times.

Provision is in particular made that the elevated portions are interrupted in the peripheral direction by notches which are in particular designed as milled slots and which in particular extend up to the axial rear end of the screw head.

The axial rear end of the screw head is to be understood as the free end of the screw head.

As will be explained below, provision is in particular made that the notches have flanks inclined in the peripheral direction in order thus in particular to achieve a pyramid shape or hipped roof shape of the elevated portions. In accordance with a first embodiment, the notches can extend along the longitudinal extent of the bone screw, i.e. axially, or can be designed as inclined in the peripheral direction. Provision is in particular made that a plurality of such notches are provided, in particular more than six, in particular twelve or more than twelve. Provision is in particular made in this respect that the flanks of the flank structure sections extending in the peripheral direction and in particular each bounding a groove are (also) inclined toward one another.

Provision is in particular made that, as explained, the elevated portions have two further inclined flanks in addition to the two (upper and lower) flanks inclined toward one another and extending in the peripheral direction, with the surface sides of these flanks facing in the peripheral direction and each bounding a notch. These two flanks can extend in a straight manner in the radial direction or can in particular be inclined toward an elevated portion center so that a pyramid shape or hipped roof shape of the elevated portions results in dependence on the peripheral extent of the elevated portion, in particular when the notches extend axially, i.e. are not inclined in the peripheral direction. With notches inclined in the peripheral direction, a pyramid shape or hipped roof shape displaced in accordance with their outline results, with the outline of the elevated portion being substantially of parallelogram shape when it is neglected that the periphery of the enveloping contour increases toward the rear end of the screw head due to the concave design.

Provision is in particular made that the flanks of the at least one flank structure section respectively bounding a notch are inclined toward one another at an angle from an angular range between 40° and 120°, in particular of approximately 60°.

A pyramid shape or a hipped roof shape in particular improves the fast engagement on the screwing in of the screws and facilitates it. In addition, a breakout of the screw is ideally avoided and an ideal force distribution results. Lever forces on the screwing in of the screw which would typically result in a screw centration are ideally avoided by the provision of a pyramid shape or hipped roof shape. Furthermore, an explantation of the screw is facilitated by a pyramid shape or hipped roof shape since the individual pyramids or hipped roofs mill their own path through the anchorage.

To avoid ruptures or inflammation of soft organs and sinews, it has been found to be advantageous to form a rearmost edge of the screw head in rounded form.

The invention also relates to an implant system.

The passage opening can either be provided with an internal thread, in particular with a metric thread such as an M3 thread, or with at least one flank ring, preferably only one flank ring, projecting radially inwardly, to enter into blocking interaction with the elevated portions of the bone screw.

The material of the bone plate is preferably softer than the material for the bone screw. A deformation or shaping of the internal thread or of the at least one flank ring of the passage opening consequently occurs by the flank structure section or by the elevated portion or elevated portions at the head of the bone screw on the screwing of the bone screw into the passage opening. The cooperating structures of the screw head and of the passage opening can in particular be formed with respect to shape and material selection such that a cold welding or a connection similar to a cold welding occurs between the screw head and the passage opening when the screw is screwed into the passage opening.

The cooperating structures of the screw head and of the passage opening are in particular formed with respect to shape and material selection such that, despite the good connection between the screw head and the passage opening, this connection can be released again and the screw can be screwed into the passage opening one further time or a plurality of further times.

The system in accordance with the invention is a so-called polyaxial implant system or fixation system which makes it possible to screw the bone screws into the passage openings of the bone plate in each case at any desired angle and to realize an angle stable arrangement of the bone screw relative to the bone plate.

The passage opening can be provided with a depression only at one side or at both sides.

To achieve a particularly high stability of the connection, it has been found to be advantageous to provide the passage opening with at least one notch extending in the direction of the longitudinal extent of the passage opening. The passage bore is in particular milled out in star shape. The notches can have the same depth extent or can have a depth extent differing from one another. It is also conceivable that the depth extent, i.e. the radial extent, of the notches is constant or varies over the axial extent in the case of a slanted notch progression.

Provision is preferably made that the passage opening and/or the at least one notch is cylindrical, i.e. does not taper.

Provision is furthermore preferably made that the at least one longitudinal notch has a partly circular cross-section in a plane which extends perpendicular to a longitudinal axis of the passage opening.

Provision is in particular made that the passage opening of the bone plate has at least two axially adjacent flank rings whose inner diameters differ from one another.

Figure 11:
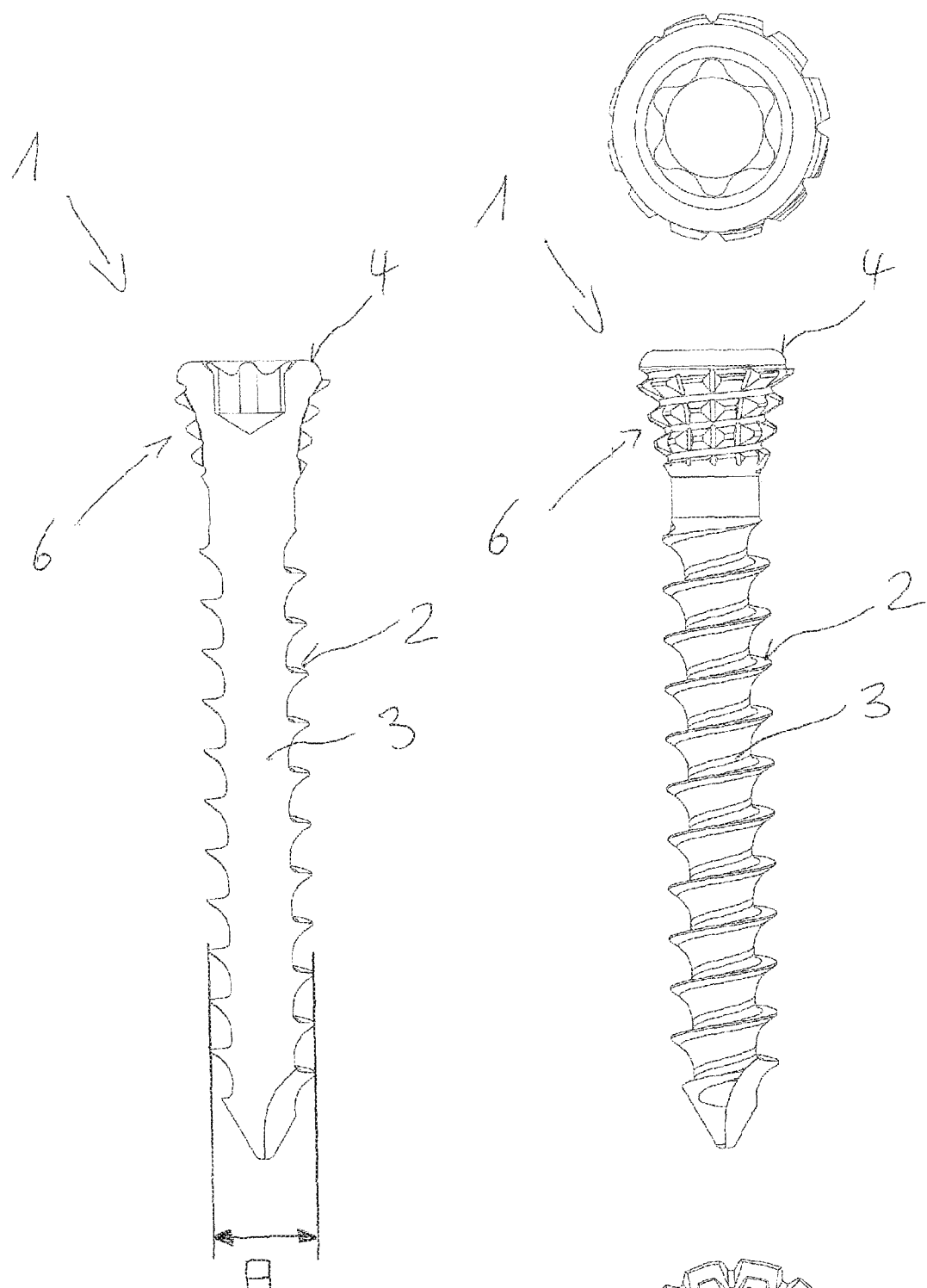
Figure 12:
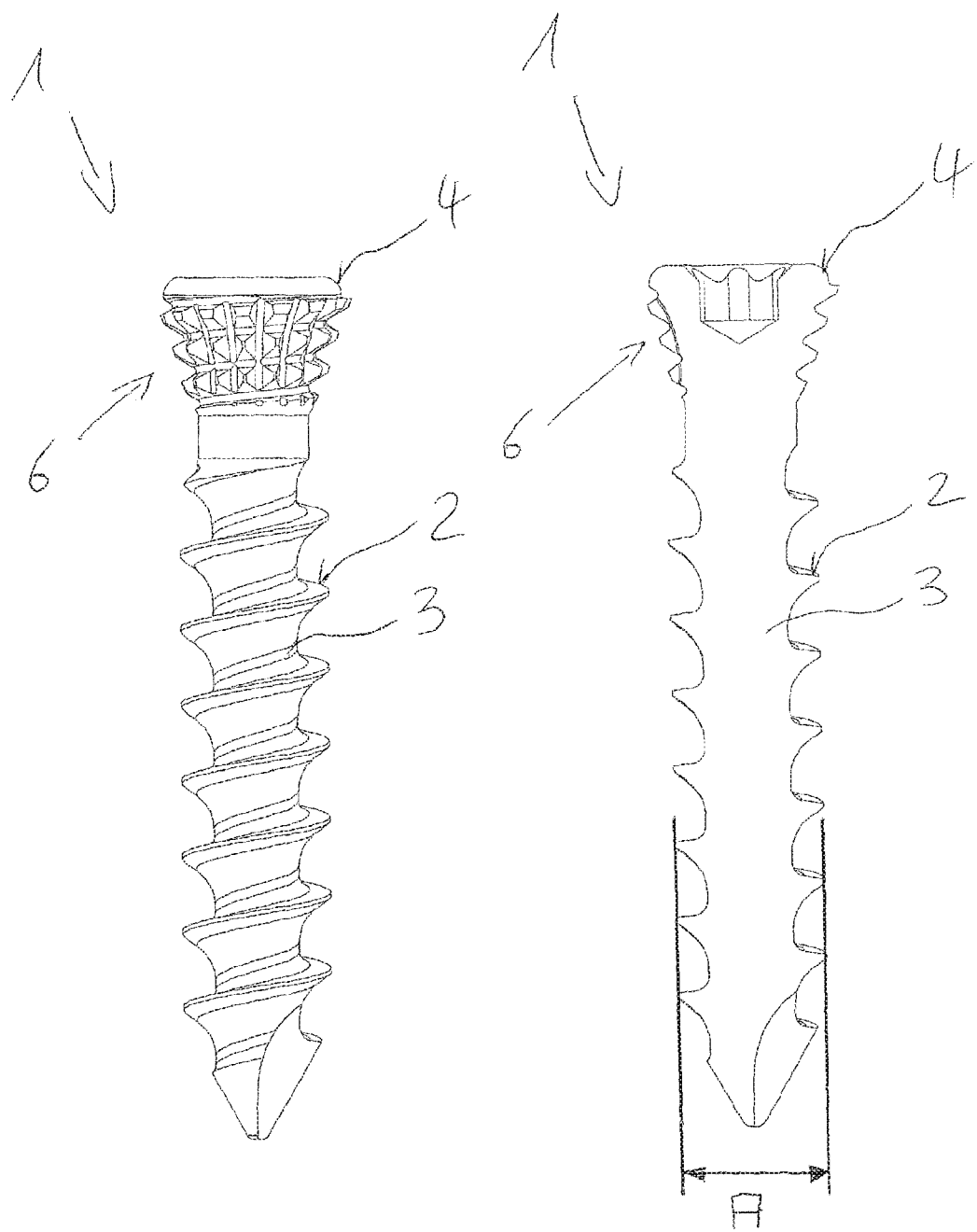
Figure 13:
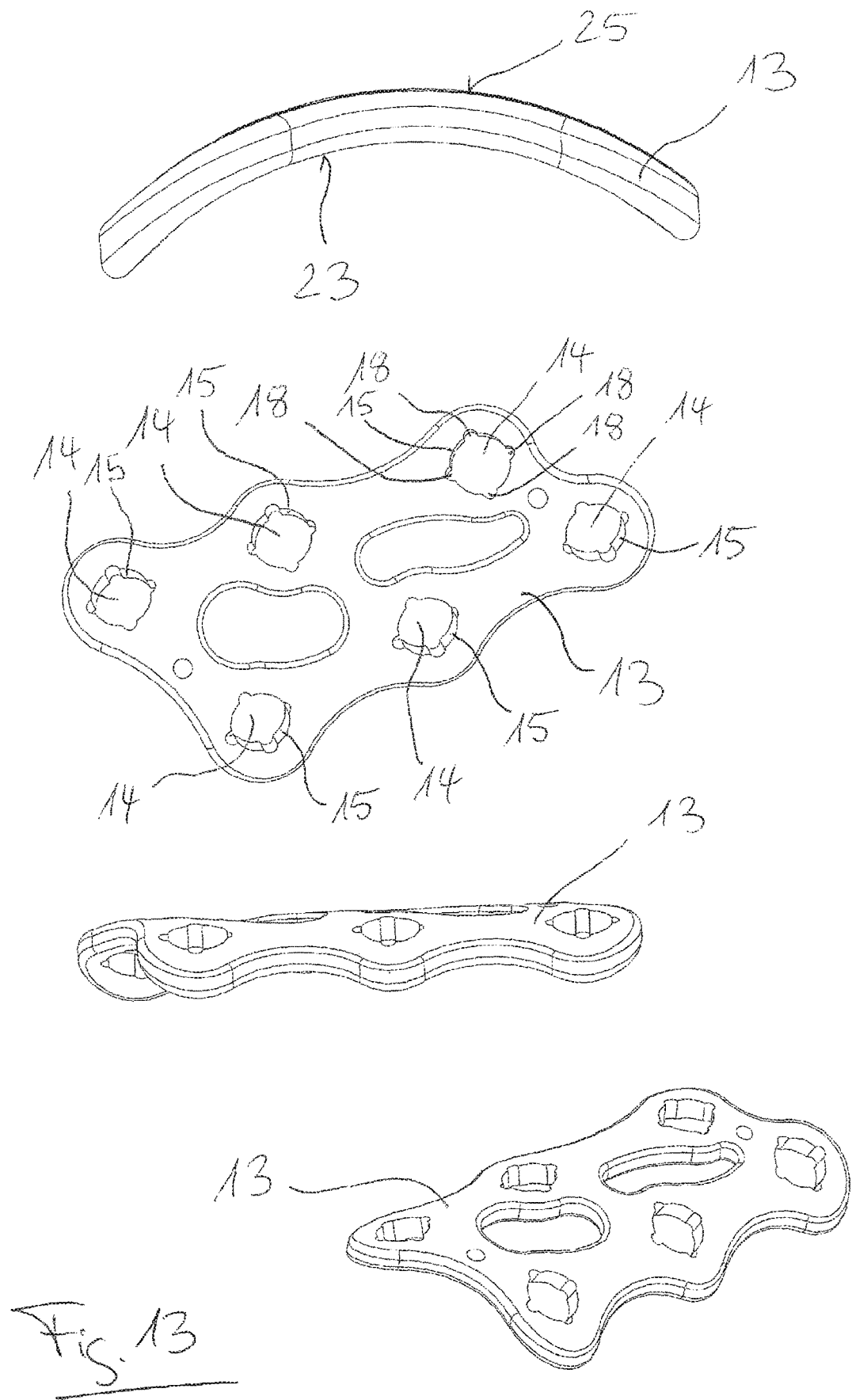

Further advantages, features and details of the invention result from the description of possible embodiments and with reference to the drawings. They show:

FIG. 1 an upper section of a bone screw having a concave enveloping contour and having a coiled flank structure section which bounds a coiled thread groove at both sides;

FIG. 2 an alternative embodiment of a screw in which a plurality of circular flank structure sections are provided which are arranged in parallel with one another;

FIG. 3 a further alternative embodiment of a screw head in which notches are formed in the flank structure sections by notches inclined in the peripheral direction;

FIGS. 4-9 alternative embodiments of bones and plates for interaction with the bone screws shown in FIGS. 1 to 3, wherein the bone plates are characterized by mutually different passage opening geometries;

FIG. 10 a plan view of a bone plate having a passage opening which is provided with notches in a star-shaped manner;

FIG. 11 a further embodiment of a bone screw in accordance with the invention;

FIG. 12 a further embodiment of a bone screw in accordance with the invention;

FIG. 13 a further embodiment of a bone plate in accordance with the invention; and FIG. 14 a representation to illustrate the effect of a concave enveloping contour.

The same elements and elements having the same function are marked by the same reference numerals in the Figures.

FIG. 1 shows a surgical bone screw 1 having a shaft 3 bearing a bone thread 2 and only shown in an upper axial section. The bone screw 1 additionally has a screw head 4 in the region of its rear end region at the top in the plane of the drawing, the screw head being provided at the front face with a drive, for example, a Torx drive, not shown in the drawings. The screw head 4 is characterized by a rotationally symmetrical concave enveloping contour 5 which is shown in outline in the left half of the drawing. In the embodiment in accordance with FIG. 1, the enveloping contour has a constant progression in the axial direction; that is it can be described by a curved mathematical function rotated about a central longitudinal axis L of the bone screw 1. In the specific embodiment, it is a part arc of a circle, here having a radius R=3 mm. What is important is the concave shape which does not necessarily have to have a constant progression, but which can rather also be formed by two axially mutually engaging conical sections having a mutually different conical angle or can comprise two such conical sections.

It can be recognized that the screw head is provided with a groove structure 6 which is reminiscent of an external thread in the embodiment shown.

The groove structure 6 in this respect has a coiled (raised) flank structure section 7, i.e. a flank structure section having a pitch, which extends a multiple of times about the periphery of the screw head. It can be recognized that the flank structure section 7 is interrupted, at regular intervals here, and indeed by notches 8 extending in an axial direction along the bone screw 1, wherein each notch 8 passes through the coiled flank structure section 7 a multiple of times (at different axial levels) so that overall both a plurality of elevated portions 9 spaced apart in the peripheral direction and a plurality of elevated portions 9 spaced part in the axial direction result which have a hipped roof shape in the embodiment shown, which will be explained in the following. The elevated portions 9 form an external thread or lie on a line such as would define an external thread.

The hipped roof shape results from the fact that the two flanks 10 which extend in the peripheral direction and which respectively bound a thread groove or a turn are inclined with respect to one another. Two further flanks 11 respectively bounding a notch 8 extend substantially at right angles to these two flanks, with the two further flanks 11 of a notch likewise being inclined toward one another. Overall, all four flanks 10, 10, 11, 11 of the elevated portions are inclined toward an elevated portion center, i.e. toward one another. For the case of a larger angle of inclination of the two flanks 11 and/or for the case of a shorter peripheral extent of the elevated portions 9 due to the provision of a plurality of notches 8, the shown hipped roof shape, which is in particular provided, can also open into a pyramid shape which tapers in a more acute manner toward a point in comparison with the hipped roof shape.

The embodiment of a bone screw 1 shown in FIG. 2 substantially only differs from the previously described embodiment shown in FIG. 1 in that not only one single coiled flank structure section 7 is provided, but rather a plurality of axially adjacent flank structure sections 7 which are each located in a radial plane, that is flank structure sections without a thread pitch. The notches 8 also extend in this embodiment up to the axially rear end of the bone screw 1 and extend in an axial direction such that the hipped-roof shaped elevated portions 9 result which are bounded in the axial direction by the flanks 10 and in the peripheral direction by the flanks 11.

As also in the embodiment in accordance with FIG. 1, a rearmost edge 12 of the bone screw 1 is designed as rounded to avoid tissue injuries.

The embodiment of the bone screw 1 shown in FIG. 3 in turn only differs from the embodiment shown in FIG. 2 in that the notches 8 do not extend straight in the axial direction, but are rather inclined in the peripheral direction, whereby the outlines of the hipped-roof shaped notches 9 are displaced in the manner of a parallelogram. The embodiment in accordance with FIG. 3 can also be formed, alternatively to the plurality of flank structure sections 7, with a single coiled flank structure section 7, as shown in FIG. 1.

Differently designed bone plates 13 are shown in FIGS. 4 to 9 and each have a passage opening 14 for a bone screw in accordance with the invention. FIG. 4 shows the simplest case of a bone plate having an axially throughgoing internal thread 15.

The embodiment in accordance with FIG. 5 has, in addition to the internal thread 15, a depression 16 for the bone screw head at only one side.

The embodiment in accordance with FIG. 6 has a respective depression 16 at both sides. In the embodiment shown, the internal thread 15 is reduced by way of example to a single turn, with an embodiment having a plurality of turns also being possible.

The embodiment of a bone plate 13 in accordance with FIG. 7 does not have any internal thread, but rather two flank rings 17 closed peripherally and spaced apart axially (alternatively, more than two flank rings can also be anchored or provided).

In the embodiment in accordance with FIG. 8, an internal thread is likewise not provided, but rather in turn two axially adjacent flank rings, with the inner diameters of the flank rings 17 differing from one another (alternatively, more than two flank rings can also be anchored or provided).

In the embodiment in accordance with FIG. 9, substantially only two depressions 16 are shown which bound a flank ring 17.

A bone plate 13 is shown in a plan view in FIG. 10. The passage opening 14 having an internal thread 15 can be recognized, wherein the passage opening 14 is provided in the region of its outer periphery with a plurality of notches 18 evenly spaced apart in the peripheral direction to improve the stability of the connection of bone screw and bone plate. The passage opening 14 and the notches 18 are cylindrical, i.e. do not taper. The notches have a part circular cross-section.

FIGS. 11 and 12 each show a complete bone screw 1 in accordance with the invention, and indeed in a front view and in a section along the central longitudinal axis, wherein the outer diameter A of the shaft 3—that is measured at the bone thread 2—in the screw 1 in FIG. 11 has a value of 2.7 mm and in the screw 1 in FIG. 12 has a value of 3.5 mm. The groove structure 6 at the screw head 4 is here respectively provided in the form of a thread, i.e. the elevated portions of the groove structure 6 form a peripheral turn. The notches each extend in parallel with the central longitudinal axis. Furthermore, a plan view of the screw head 2 is shown at the top right and a plan view of the tip of the screw 1 is shown at the bottom right in FIG. 11—enlarged with respect to the front view and the sectional view.

FIG. 13 shows an example for a bone plate 13 having here six passage openings 14 into which a respective bone screw 1 in accordance with the invention can be screwed.

The elevated portions 9 forming the groove structure 6 at the screw head 4 in this respect cooperate with an internal thread 15 of the respective passage opening 14, the internal thread being interrupted by four notches 18 evenly spaced apart from one another in the peripheral direction and having a partly circular cross-section. The elevated portions 9 of the screw head 4 cooperate in a blocking manner with the threaded sections 15 thereby formed on the screwing in of the bone screw in that the elevated portions 9 of the bone screw 1 which comprise a relatively harder material deform or shape the threaded sections 15 of the passage opening 14 comprising a relatively softer material.

The passage openings 14 are cylindrical, that is they have a constant inner diameter—apart from their internal thread 15 and the notches 18—through the bone plate 13 over their longitudinal extent.

As the side view in FIG. 13 shows, the bone plate 13 has a concave lower side 23 facing the bone in the implanted state and a convex upper side 25.

FIG. 14 illustrates that a bone screw 1 in accordance with the invention (FIGS. 14a and 14b) having a concave enveloping contour at the screw head can be screwed in without problem up to an angle which is larger than in screws not belong to the invention having a conical (FIG. 14c) or cylindrical (FIG. 14d) enveloping contour at the screw head.

The comparison of FIGS. 14b, 14c and 14d shows that at a screw-in angle selected by way of example here of 15°, the concave screw head in accordance with the invention (FIG. 14b can be screwed in without problem since sufficient "space" is present between the enveloping contour of the screw head illustrated by the contour lines 19 and the internal thread 15 of the passage opening, in particular of the edge 21 at the inlet region of the passage opening. This is not the case with the screws not in accordance with the invention. Whereas a screw with a conical head contour (FIG. 14c) may still be able to be screwed in with a high force effort, the screwing in of a screw with a cylindrical head contour (FIG. 14d) would mean damage to the screw or plate or—as already initially mentioned—would signify the risk of a self-centration or of an uncontrolled pressing away of the plate.

It can be seen from FIG. 14a that the screw 1 in accordance with the invention can also be screwed in without problem at an angle of 0°.

REFERENCE NUMERAL LIST 1 bone screw
2 bone thread
3 shaft
4 screw head
5 enveloping contour
6 groove structure
7 flank structure section(s))
8 notch(es)
9 elevated portions
10 flank(s)
11 flank(s)
12 edge
13 bone plate
14 passage opening
15 internal thread
16 depression(s)
17 flank ring(s)
18 notch(es)
19 contour line
21 edge
23 lower side
25 upper side
L central longitudinal axis
R radius
A outer diameter

The invention claimed is:

1. An angle stable implant system, comprising:
at least one bone screw including a threaded shaft and a head portion defining an enveloping contour, the head portion including a groove structure comprising at least one flank structure section extending in a peripheral direction, wherein a jacket surface of the enveloping contour includes a concave progression; and
a bone plate including a concave lower side, a convex upper side, and at least one passage opening for receiving the at least one bone screw, the at least one passage opening including:
at least one protrusion structured for engagement with the at least one bone screw; and
a plurality of notches disposed along an outer periphery of the at least one passage opening.

2. An angle stable implant system, comprising:
at least one bone screw including a threaded shaft and a head portion the head portion defining a concave enveloping contour and including elevated portions separated by axially extending notches; and
a bone plate including a concave lower side, a convex upper side, and at least one passage opening for receiving the at least one bone screw, the at least one passage opening including a plurality of notches disposed along an outer periphery of the at least one passage opening;
wherein the at least one bone screw is formed from a first material and the bone plate is formed from a second material, the first material being harder than the second material; and
wherein the elevated portions are configured to deform or reshape threaded sections of the at least one passage opening of the bone plate when the at least one bone screw is screwed into the at least one passage opening.

3. An angle stable implant system, comprising:
at least one bone screw; and
a bone plate including at least one passage opening for receiving the at least one bone screw, wherein the at least one passage opening is defined by a circular perimeter and includes at least one longitudinal notch extending along a longitudinal extent of the at least one passage opening:
wherein the at least one bone screw comprises:
a shaft including: a bone thread;
a blocking means for cooperation with the bone plate or for a direct anchorage in the bone; and
a screw head including a rotationally symmetrical enveloping contour:
wherein the blocking means include a groove structure comprising at least one flank structure section extending in a peripheral direction:
wherein a jacket surface of the enveloping contour includes a concave progression; and
wherein the flank structure section of the groove structure extending in the peripheral direction is interrupted at least once in the peripheral direction such that at least one elevated portion results for blocking cooperation with the bone plate or with the bone.

4. The system of claim 3, wherein the at least one bone screw is formed from a first material and the bone plate is formed from a second material, the first material being harder than the second material.

5. The system of claim 4, wherein elevated portions of the at least one bone screw are configured to deform or reshape threaded sections of the at least one passage opening of the bone plate when the at least one bone screw is screwed into the at least one passage opening.

6. The system of claim 3, wherein the at least one passage opening includes an internal thread.

7. The system of claim 6, wherein the internal thread comprises a metric internal thread.

8. The system of claim 3, wherein the at least one passage opening includes at least one flank ring.

9. The system of claim 8, wherein the at least one flank ring comprises only one flank ring which projects radially inwardly in a radial plane.

10. The system of claim 3, wherein the at least one passage opening includes at least two axially adjacent flank rings whose inner diameters differ from one another.

11. The system of claim 3, wherein the at least one passage opening includes at least two peripherally closed and axially adjacent flank rings.

12. The system of claim 3, wherein the at least one passage opening includes at least one depression.

13. The system of claim 12, wherein two depressions are provided which bound a flank ring.

14. The system of claim 3, wherein the at least one longitudinal notch has a part circular cross-section in a plane which extends perpendicular to a longitudinal axis of the at least one passage opening.

15. The system of claim 14, comprising a plurality of longitudinal notches evenly spaced apart from one another in a peripheral direction, wherein the at least one passage opening includes an internal thread which is interrupted by the plurality of notches.

16. The system of claim 3, wherein the bone plate includes a concave lower side and a convex upper side.

\* \* \* \* \*